United States Patent
You et al.

(10) Patent No.: US 9,023,901 B2
(45) Date of Patent: May 5, 2015

(54) SYSTEM, PROCESS AND REACTOR FOR CONDUCTING A SYNTHESIS GAS CONVERSION REACTION

(71) Applicants: Lixin You, Sugar Land, TX (US);
Shabbir Husain, Emeryville, CA (US);
Christopher M. Chen, Sugar Land, TX (US)

(72) Inventors: Lixin You, Sugar Land, TX (US);
Shabbir Husain, Emeryville, CA (US);
Christopher M. Chen, Sugar Land, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/955,897

(22) Filed: Jul. 31, 2013

(65) Prior Publication Data
US 2015/0038598 A1    Feb. 5, 2015

(51) Int. Cl.
*C07C 27/06* (2006.01)
*C07C 1/04* (2006.01)
*C10G 2/00* (2006.01)

(52) U.S. Cl.
CPC ............ *C07C 1/0485* (2013.01); *C07C 1/041* (2013.01); *C10G 2/32* (2013.01); *C07C 2523/75* (2013.01)

(58) Field of Classification Search
CPC .......................... C07C 2523/75; C10G 2/32
USPC .................................................. 518/700, 715
See application file for complete search history.

(56) References Cited

U.S. PATENT DOCUMENTS

| 4,181,675 | A | 1/1980 | Makin et al. |
| 8,206,667 | B2 | 6/2012 | Najafi et al. |
| 8,425,854 | B1 | 4/2013 | Husain et al. |
| 2004/0181313 | A1 | 9/2004 | Mohedas et al. |
| 2009/0170964 | A1* | 7/2009 | Fayyaz Najafi et al. ...... 518/700 |
| 2011/0160315 | A1 | 6/2011 | Kibby et al. |

OTHER PUBLICATIONS

PCT/US2012/030932, International Search Report, mailing date Sep. 25, 2012, pp. 1-8.

* cited by examiner

*Primary Examiner* — Sudhakar Katakam
(74) *Attorney, Agent, or Firm* — Karen R. DiDomenicis

(57) ABSTRACT

A synthesis gas conversion process and system are disclosed. Fresh syngas from a methane reformer is used as a sweep zone gas feed which is caused to flow across a water perm-selective membrane in a membrane reactor. The water perm-selective membrane is adjacent a synthesis gas conversion reaction zone in which synthesis gas is contacted with a catalyst and converted to effluent including water. Water is removed from the reaction zone through the membrane and passes out of the reactor with the sweep zone gas. The water is then removed from the sweep zone gas forming a modified gas feed which is fed to the reaction zone. The modified gas feed has a preferred $H_2/CO$ ratio to feed into the reaction zone.

8 Claims, 9 Drawing Sheets

SYSTEM, PROCESS AND REACTOR FOR CONDUCTING A SYNTHESIS GAS CONVERSION REACTION

FIELD

The present invention relates to methods wherein water and hydrocarbon products are produced as part of a synthesis gas conversion and the water is removed in situ from the reaction products using a membrane. The present invention further relates to an integrated system including synthesis gas generation and a Fischer-Tropsch reactor using a membrane for in situ water removal, reactant supplementation, and modifying the synthesis gas ratio.

BACKGROUND

Removal of water is a key issue to be addressed in synthesis gas conversion reactions. For instance, water is a primary by-product in a Fischer-Tropsch (FT) reaction and its presence is generally detrimental to the overall efficiency of the FT reaction. In an FT reaction, a synthesis gas mixture of carbon monoxide (CO) and hydrogen gas ($H_2$), referred to hereinafter as "syngas," is converted in the presence of an FT catalyst (most commonly iron- or cobalt-based) into hydrocarbon products, water and other byproducts. The syngas may be generated from a number of carbon containing sources such as natural gas, coal or bio-mass. It is often desirable to convert these carbon sources into a liquid hydrocarbon mixture from their original gas or solid states.

As the FT reaction occurs at relatively high temperature, the water produced is generally in the form of water vapor. Produced water vapor reduces the partial pressures of FT reactants, thus affecting reaction kinetics and reducing reaction rates. Water vapor is also detrimental to the life of FT catalysts, and especially at high partial pressures, leads to the oxidation of the catalyst and the sintering of the catalyst support, resulting in a reduction in the catalyst activity. Conventional FT fixed bed reactors separate water from other reaction products and unreacted CO and $H_2$ gas after they exit the reactor's outlet. Due to these adverse effects of water on the FT reaction, conventional FT fixed bed reactors have a relatively low per pass CO conversion to limit high water partial pressures in the reactor. The unreacted CO is often recycled back to an FT reactor inlet so that it may again potentially be converted into a hydrocarbon, at the cost of increased throughputs, resulting in larger reactors.

Efforts with respect to in situ dehydration in conversion of syngas to hydrocarbon products and water have been described. U.S. Pat. No. 8,206,667 B2 (Fayyaz-Najafi et al.), assigned to Chevron U.S.A. Inc., hereby incorporated by reference in its entirety, describes improved designs for FT reactors, in which water is removed in situ using a membrane and wherein heat management issues are also addressed Another issue to be addressed in synthesis gas conversion reactions is control of the ratio of hydrogen to carbon monoxide ($H_2$/CO) in the syngas, as this affects the product distribution. When this ratio is too high, reaction products include undesirably high levels of methane and light gas. When this ratio is too low, reaction products include undesirably high levels of olefin and oxygenates. Additionally, consumption of hydrogen and CO in the FT reactor occurs rapidly in the initial or upstream section of the reactor thereby lowering the partial pressures of hydrogen and CO and thus the reaction rate and the $H_2$/CO ratio in the downstream section of the reactor. Although the downstream end of the reactor has available heat removal capacity, this capacity remains unused when this section of the reactor is reactants ($H_2$ and/or CO) starved. U.S. Pat. No. 8,425,854 B1 (Husain et al.), assigned to Chevron U.S.A. Inc., hereby incorporated by reference in its entirety, describes a synthesis gas conversion process in which a hydrogen-containing sweep gas is caused to flow across a water permselective membrane adjacent a synthesis gas conversion reaction zone. The sweep gas has sufficient hydrogen partial pressure to cause hydrogen to pass through the membrane into the reaction zone.

It would be desirable to provide an improved process for the in situ removal of water from a synthesis gas conversion reactor such as an FT reactor. It would be further desirable to simultaneously provide for the addition of hydrogen and CO at a controlled rate along the length of such a reactor to maintain sufficiently high hydrogen to carbon monoxide ratio and reactant concentrations to overcome the aforementioned current design constraints, thereby increasing the productivity of the reactor.

SUMMARY

In one aspect, the present invention relates to a synthesis gas conversion process including passing a sweep zone gas feed comprising hydrogen and carbon monoxide having a hydrogen to carbon monoxide ratio of greater than 2 into a reactor, over the sweeping side of a membrane and out of the reactor. Hydrogen and carbon monoxide pass from the sweep zone gas feed into the reaction zone from the sweeping side of the membrane and water passes from the reaction zone through the membrane into the sweep zone gas feed, then removed from the reactor with the sweep zone gas. Water is then separated from the sweep zone gas removed from the reactor to form a modified gas feed having a hydrogen to carbon monoxide ratio of less than 1.7. The modified gas feed is then contacted with the synthesis gas conversion catalyst in the reaction zone to form reaction products including water.

The reactor includes a sweep zone gas feed inlet and a sweep zone gas outlet in fluid communication with the sweep zone gas feed inlet; a water inlet and a steam outlet in fluid communication with the water inlet; a reaction zone for containing synthesis gas conversion catalyst in which hydrogen and carbon monoxide react to form reaction products including water; a products outlet in fluid communication with the reaction zone; and a membrane having a reactant side contacting the reaction zone and a sweeping side opposite the reactant side.

The sweep zone gas feed is formed in a methane reformer having an outlet connected to the sweep zone gas feed inlet. The hydrogen to carbon monoxide ratio of the sweep zone gas feed from the methane reformer is greater than 2. Tail gas separated from the reaction products can be recycled to the methane reformer. No gas is recycled from the reaction products to the reaction zone.

In another aspect, the present invention relates to a system including a synthesis gas conversion reactor including a housing having a sweep zone gas feed inlet and a sweep zone gas outlet in fluid communication with the sweep zone gas feed inlet, a modified gas feed inlet and a reaction products outlet in fluid communication with the modified gas feed inlet, a water inlet and a steam outlet in fluid communication with the water inlet; and a membrane within the housing which defines a reaction zone and a sweep zone, wherein the reaction zone is adapted to convert synthesis gas into products including hydrocarbons and water in the presence of a synthesis gas conversion catalyst, wherein the membrane allows the water to permeate from the reaction zone to the sweep zone and a sweep zone gas feed to permeate from the sweep zone to the reaction zone. The system further includes a gas-water separator connected to the reactor in fluid communication with and between the sweep zone gas outlet and the modified gas feed inlet. The system includes no compressor for recycling of gas from the gas-water separator to the modified gas feed inlet. The system can include a methane reformer for reforming methane-containing gas to form the sweep zone gas feed comprising hydrogen and carbon monoxide having a hydrogen to carbon monoxide ratio of greater than 2 wherein the methane reformer has an outlet connected to the sweep zone gas feed inlet.

BRIEF DESCRIPTION OF THE DRAWINGS

These and other objects, features and advantages of the present invention will become better understood with regard to the following description, appended claims and accompanying drawings where:

DETAILED DESCRIPTION

Figure 1A:
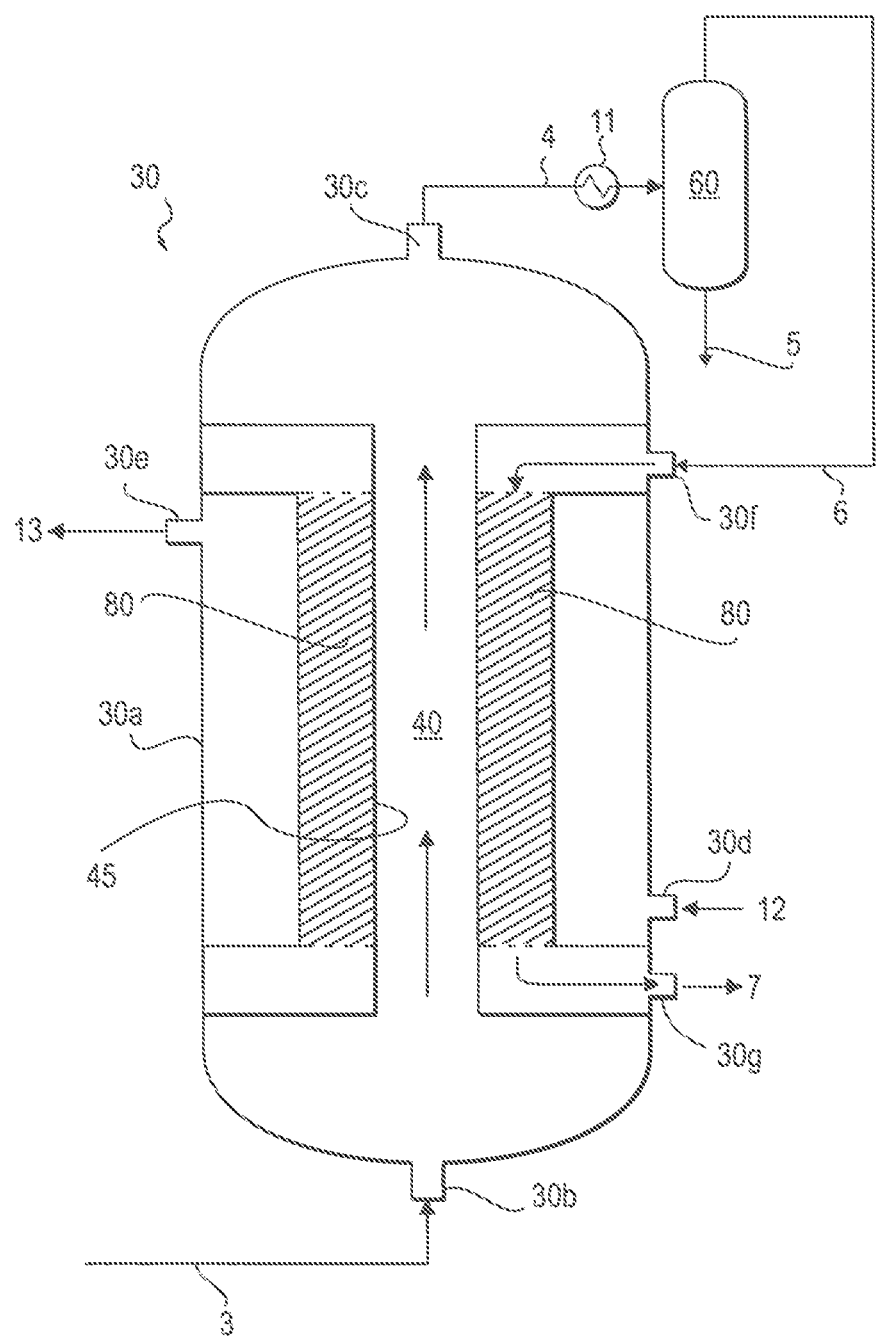
FIGS. 1A-1E are schematic illustrations of membrane reactors according to five alternative embodiments of the invention.

In one embodiment, as illustrated in FIG. 1A, a reactor 30 includes a housing 30a having a sweep zone gas feed inlet 30b, a sweep zone gas outlet 30c in fluid communication with the sweep zone gas feed inlet 30b, a water inlet 30d and a steam outlet 30e in fluid communication with the water inlet 30d, and a syngas feed inlet 30f and a products outlet 30g. Within the reactor is a reaction zone 80 in fluid communication with the products outlet 30g for containing synthesis gas conversion catalyst in which hydrogen and carbon monoxide of a syngas feed react to form reaction products 7 also referred to as effluent. Reaction products 7 can include light gas, liquid hydrocarbon products of varying carbon chain lengths, $CO_2$ and water and a variety of other compounds. The reaction zone 80 can be within a fixed bed reactor tube loaded with synthesis gas conversion catalyst. Adjacent the reaction zone 80 is a water permselective membrane 45 having a reactant side facing the reaction zone 80 and a sweeping side opposite the reactant side facing a sweep zone 40. By "water permselective membrane" is meant a membrane which allows water to pass there through preferentially relative to other liquid and gas components. The membrane 45 thus defines a reaction zone 80 and a sweep zone 40. The reaction zone 80 is adapted to convert synthesis gas 6 into products 7 including hydrocarbons and water in the presence of a synthesis gas conversion catalyst, i.e., a catalyst containing a Fischer-Tropsch (FT) active metal. The membrane 45 allows water to permeate from the reaction zone 80 to the sweep zone 40 and a sweep zone gas feed 3 to permeate from the sweep zone to the reaction zone. Under these conditions, the water is in the form of water vapor. Accordingly, water vapor preferentially passes through the water permselective membrane 45 as a permeate stream while the other reaction products and unreacted feed preferentially remain in the reaction zone 80 and are eventually discharged as a part of a retentate stream 7 through the downstream end of the reactor 30. The membrane 45 allows water vapor to readily pass there through from the reaction zone 80 while inhibiting the passage of other reactants and products.

FIG. 1A illustrates an embodiment in which the sweep zone gas feed 3 and the modified gas feed 6 flow in counter-current directions. In another embodiment, illustrated in FIG. 1B, an embodiment is illustrated in which the sweep zone gas feed 3 and the modified gas feed 6 flow in co-current directions.

The disclosed process provides a synthesis gas conversion process including passing a sweep zone gas feed 3 comprising hydrogen and carbon monoxide having a hydrogen to carbon monoxide ratio of greater than 2 into the reactor 30 through the sweep zone gas feed inlet 30b, over the sweeping side of the membrane 45 and out of the reactor through the sweep zone gas outlet 30c, thereby providing for the in situ removal of water from the reactor. Hydrogen and carbon monoxide pass from the sweep zone gas feed 3 into the reaction zone 80 from the sweeping side of the membrane 45 and water passes from the reaction zone 80 through the membrane 45 into the sweep zone gas and is then removed from the reactor with the sweep zone gas as stream 4. Stream 4 passes through a cooler 11. In a condenser 60, water 5 is then separated from the sweep zone gas removed from the reactor to form a modified gas feed 6 advantageously having a hydrogen to carbon monoxide ratio of less than 1.7. The modified gas feed 6 is then fed through the syngas feed inlet 30f and contacted with the synthesis gas conversion catalyst in the reaction zone 80 to form the reaction products 7.

Figure 1B:
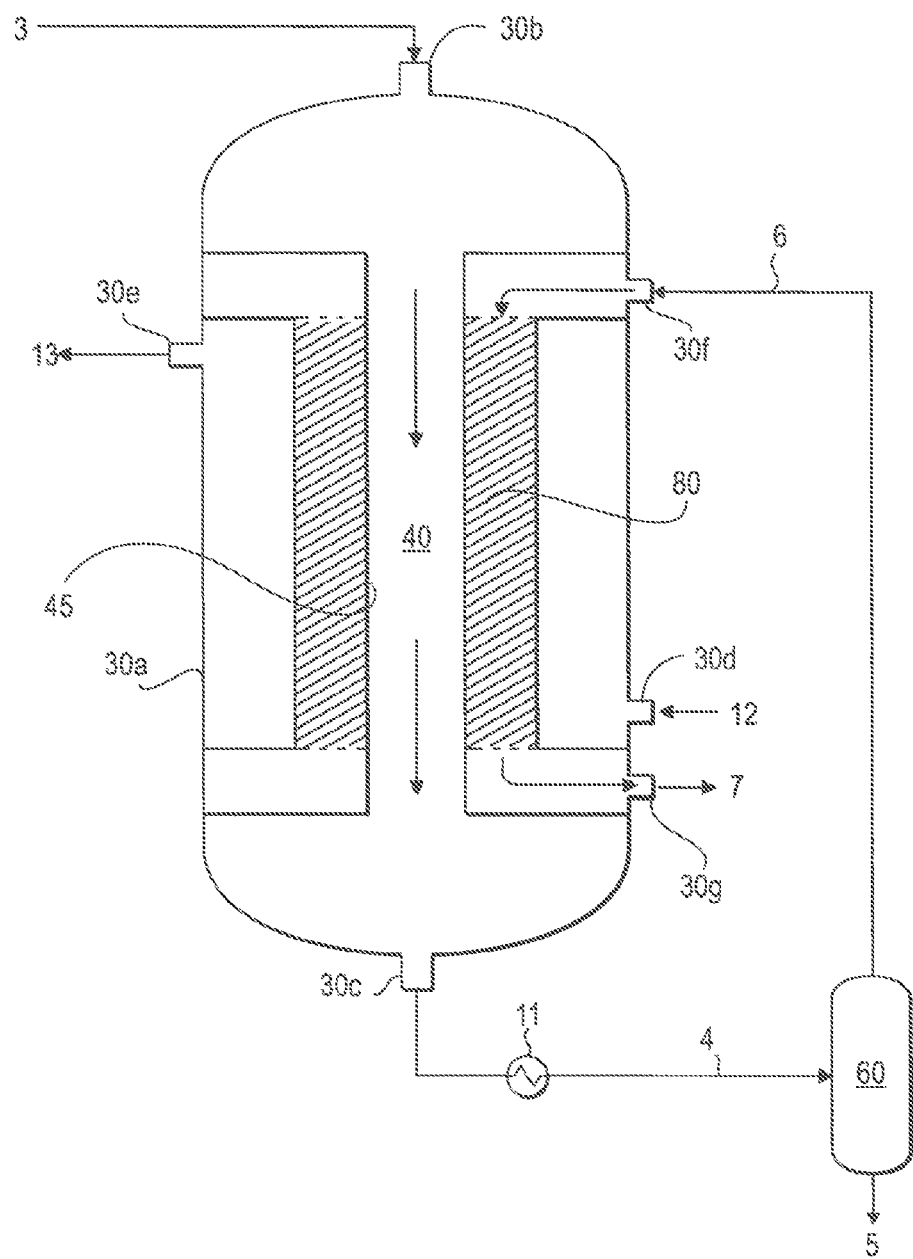
Figure 1C:
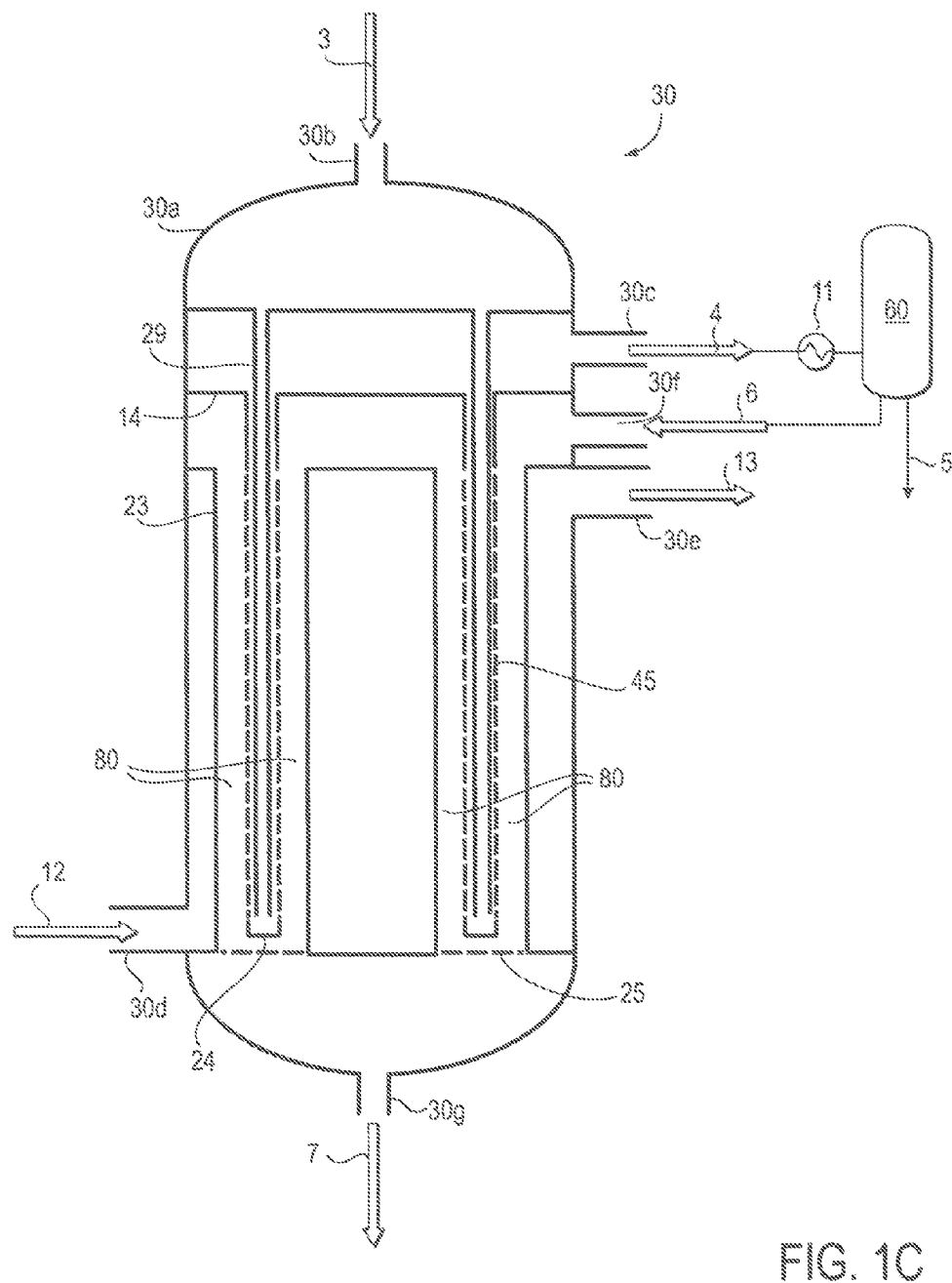

In one embodiment, as shown in FIG. 1C and described hereinafter, the reaction zone 80 is located within a fixed bed reactor tube in which the synthesis gas conversion catalyst occupies an annular volume within the tube which is bounded on the outside by the wall of the reactor tube and on the inside by a membrane tube formed by the membrane 45. This is also referred to as a double tube-in-tube reactor design (tube in a tube in a tube). The membrane tube has an outer retentate side and an inner permeate side. In this embodiment, sweep zone gas feed 3 is supplied through a pipe or conduit 29 extending into the membrane tube such that the sweep zone gas is caused to flow inside the membrane tube, between the conduit and the membrane tube. In one embodiment, the disclosed process further provides for the addition of hydrogen to the reactor. In this embodiment, the sweep zone gas has a hydrogen partial pressure sufficiently high to cause hydrogen to pass from the permeate side through the membrane to the desired location in the reaction zone. The double tube-in-tube reactor design as described above and shown in FIG. 1C can be used. While the figure illustrates two tubes, it will be understood by those skilled in the art that the reactor may include many such tubes. By adding hydrogen to the reaction zone along the length of the reactor, a more constant $H_2/CO$ ratio can be maintained along the length of the reactor. The rate of hydrogen addition can be controlled by adjusting the hydrogen partial pressure driving force across a given membrane.

One embodiment of an FT reactor having a water removal membrane 45 and utilizing a hydrogen-containing sweep zone gas feed 3 is shown in FIG. 1C. The sweep zone gas feed 3 enhances the in situ water vapor removal from the reaction zone 80. Catalyst (not shown) is packed into a reaction zone 80 formed between tubes 23 and 45. Partially mounted in the reactor 30 is a membrane assembly 14 which has multiple tubes with porous walls 45 and an end plate 24 which seals the tubes, thereby defining a water vapor zone. Membrane materials, such as a zeolite membrane, are affixed to a support wall to permit water vapor to readily pass from reaction zone 80, through water permselective material or membrane 45 and into the water vapor zone. The top of membrane assembly 14 is a tube sheet (i.e., a circular plate with multiple holes drilled with specific pattern to accommodate the membrane tubes). By way of example and not limitation, the outer diameter of tube 23 can be, for example, in the range of 1.05-2.375 inches (2.7-6.0 cm), and even 1.315-1.9 inches (3.3-4.8 cm). The outer diameter of tube 45 can be in the range of 0.675-1.9 inches (1.7-4.8 cm), and even 0.84-1.66 inches (2.1-4.2 cm).

An outer shell 30a provides a water bath chamber, surrounding the reaction zone 80. Water 12 is introduced into cooling water inlet 30d and surrounds reaction zone 80 to maintain the temperature in reactor 30 at a predetermined temperature. Heat supplied from reaction zone 80 transforms the water into steam 13 which exits the reactor by way of steam outlet 30e. Water inlet 30d and steam outlet 30e are in fluid communication with the water chamber. Controlling the water flow and the pressure and boiling temperature of the water in the water bath chamber allows the temperature in reaction zone 80 to be controlled.

A sweep zone gas assembly 29 is provided for introducing a sweep zone gas feed 3 into the water vapor zone within each membrane tube 45. Sweep zone gas assembly 29 has multiple conduits which are inserted into the water vapor zone within each membrane tube 45 and serve to deliver sweep zone gas feed 3 to the lower end of the water vapor zone. Sweep zone gas assembly 29 is in fluid communication with a sweep zone gas feed inlet 30b.

A significant portion of the water vapor produced in the reaction zone 80 passes through membrane 45 into the water vapor zone on the inner permeate side of each membrane. The partial pressure of water in the water vapor zone is maintained at a relatively low value compared to reaction zone 80, in part due to the sweep zone gas. Sweep zone gas feed 3 is introduced into sweep zone gas feed inlet 30b; passes inside the sweep zone gas feed conduits of sweep zone gas assembly 29 to the lower end of each water vapor zone; and then flows counter current to the syngas feed 6 along membrane 45 to assist in the removal of water vapor. The sweep zone gas feed 3 contains reactant synthesis gas. The combined water vapor and sweep zone gas steam 4 is then swept out of the reactor by way of water vapor outlet 30c. Stream 4 then passes through a cooler 11. In a condenser 60, water 5 is then separated from the sweep zone gas removed from the reactor 30 to form a modified gas feed 6 advantageously having a hydrogen to carbon monoxide ratio of less than 1.7. The modified gas feed 6 is then fed through the syngas feed inlet 30f and contacted with the synthesis gas conversion catalyst in the reaction zone 80 to form the reaction products 7 which exit the reactor through products outlet 30g. The reaction zone 80 can be contained at the lower end by perforated plate 25.

Figure 1D:
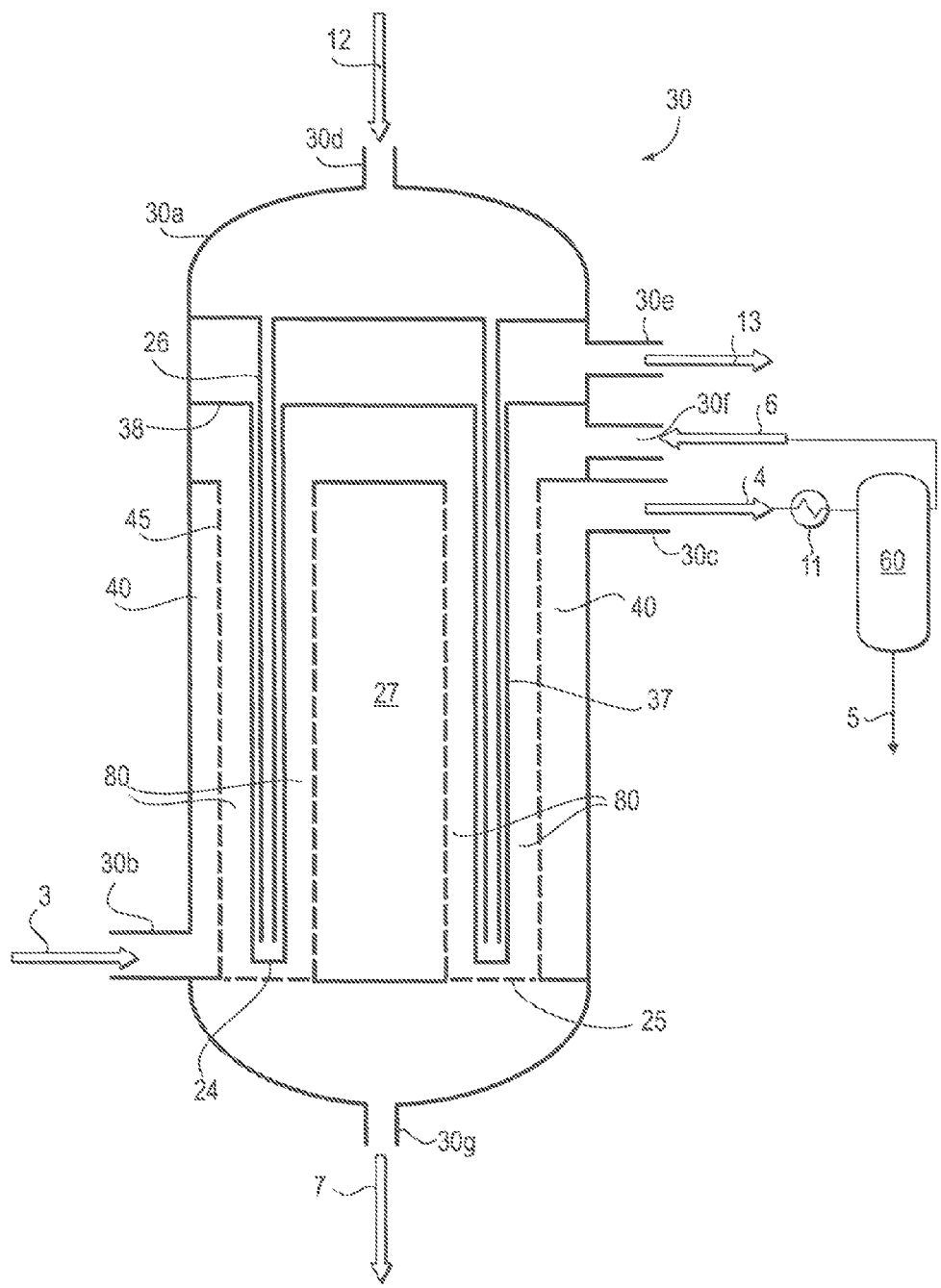

In an alternative embodiment, as shown in FIG. 1D, reactor 30 operates in a similar manner as reactor 30 described above and illustrated in FIG. 1C, except that in this embodiment, the location of the cooling water and the sweep zone gas relative to the reaction zone are reversed, such that the cooling water cools from an internal space within each reaction zone 80 and the sweep zone gas passes across the membrane tube 45 which is disposed about each reaction zone 80. Sweep zone gas feed 3 enters through sweep zone gas feed inlet 30b and flows through sweep zone 40, across the outer surface of membrane tube 45, and exits as gas stream 4 through sweep zone gas outlet 30c. Again, stream 4 then passes through a cooler 11. In a condenser 60, water 5 is then separated from the sweep zone gas removed from the reactor 30 to form a modified gas feed 6 advantageously having a hydrogen to carbon monoxide ratio of less than 1.7. The modified gas feed 6 is then fed through the syngas feed inlet 30f and contacted with the synthesis gas conversion catalyst in the reaction zone 80 to form the reaction products 7 which exit the reactor through products outlet 30g. The reaction zone 80 can be contained at the lower end by perforated plate 25.

A cooling water assembly is provided for introducing cooling water 12 into the internal space within each reaction zone 80. Cooling water assembly conduits 26 are inserted into the internal space within each reaction zone 80 and serve to deliver cooling water 12 to the lower end of the reaction zone 80. The internal space within each reaction zone 80 is defined by conduit 37 of tube sheet assembly 38. Cooling water assembly 26 is in fluid communication with a cooling water inlet 30d. Cooling water stream 13 exits through cooling water outlet 30e.

Figure 1E:
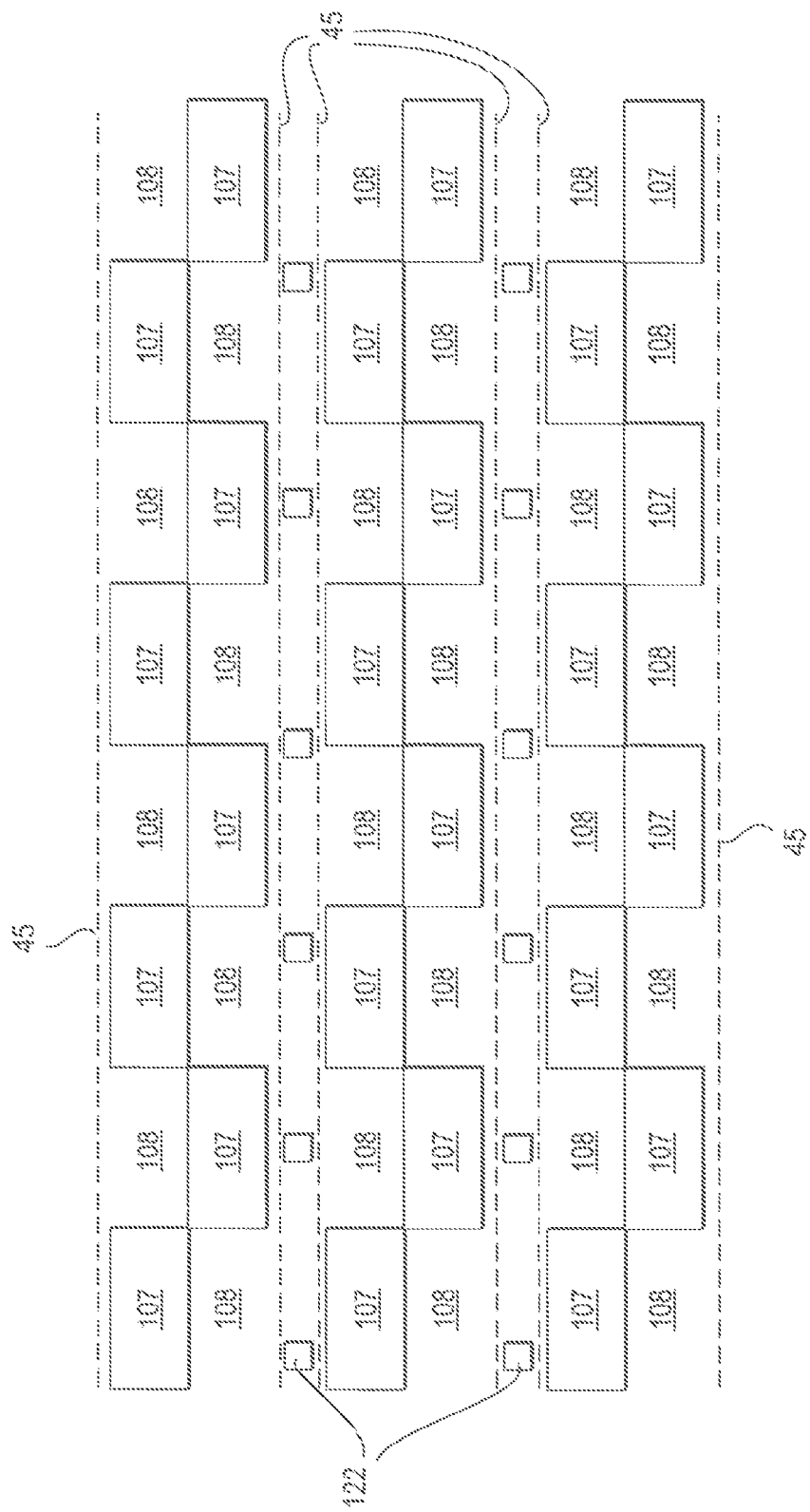

In yet another alternative embodiment, as shown in FIG. 1E, the reactor is in the form of a plate type reactor. A cross-section is illustrated. Reaction zone 108 is in the form of a channel located within the plate type reactor having multiple alternating layers of reaction zone channels 108, cooling channels 107 and water permselective membranes 45. Each layer is kept separated by porous spacers 122. Syngas feed is introduced to the reaction zone channels 108 which contain catalyst. Reaction products including water are produced in reaction zone channels 108, and water is removed across membranes 45. In this embodiment, hydrogen sweep zone gas is introduced across the face of membranes 45. Water or another suitable coolant occupies cooling channels 107, thus controlling the temperature of reaction zone channels 108. FIGS. 1A-1E illustrate only five of many possible configurations, as would be apparent to one skilled in the art. Again, the sweep zone gas stream can be removed from the reactor, passed through a cooler 11 and sent to a condenser where water is separated from the sweep zone gas. As a result, a modified gas feed advantageously having a hydrogen to carbon monoxide ratio of less than 1.7 is formed and then fed through the reaction zone channels 108 of the reactor to form the reaction products.

Figure 2:
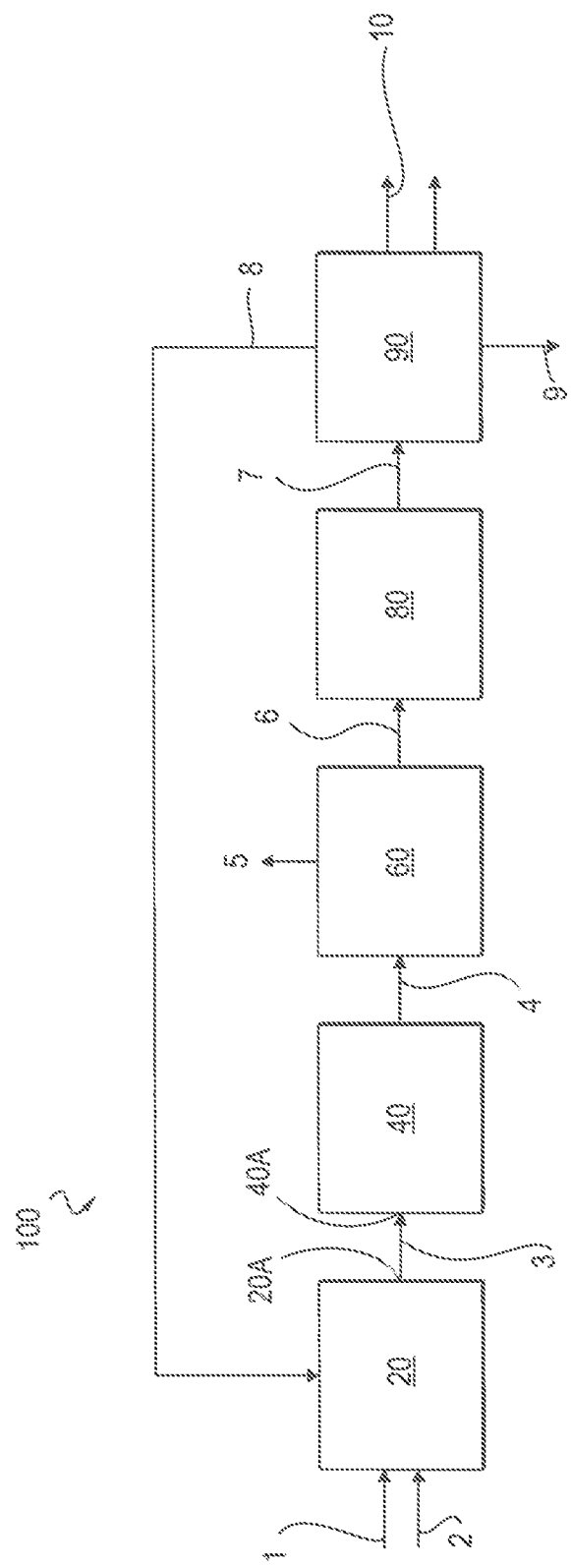
FIG. 2 is a schematic drawing of an integrated system according to another embodiment of the invention.

In one embodiment, as illustrated in FIG. 2, an integrated system 100 is provided including a methane reformer 20 for forming synthesis gas 3 which can be used as the sweep zone gas feed in the reactor. By methane reformer is meant any reformer that generates synthesis gas, also referred to as syngas, from any methane-containing gas such as natural gas. Alternatively, a syngas generator useful for generating syngas from a biomass feed or a coal feed can also be used in place of the methane reformer. In one embodiment, the methane reformer 20 receives a natural gas stream 1 and an oxygen stream 2 and forms synthesis gas containing hydrogen and carbon monoxide. The reformer 20 has an outlet 20A connected to the inlet 40A to the sweep zone 40 (the sweeping side of the membrane reactor). The hydrogen to carbon monoxide ratio of the sweep zone gas feed 3 from the methane reformer 20 is greater than 2.0. Once the sweep zone gas feed 3 passes over the sweeping side of the membrane, a stream 4 of sweep zone gas including water goes to a condenser 60 where water 5 is removed. The condenser 60 is connected to the reactor in fluid communication with and between the sweep zone gas outlet and the modified gas feed inlet. A modified syngas stream 6 is thus formed having a hydrogen to carbon monoxide ratio of less than 1.7. The modified syngas stream 6 is delivered to the reaction zone 80 (the reactant side of the membrane reactor), where the modified syngas stream 6 contacts the FT catalyst. An effluent stream 7 is removed from the membrane reactor, and effluent components are separated in an upgrader 90. Tail gas 8 is recycled to the reformer 20. Water 9 can be separated. Liquid products 10 can be separated. The liquid products may include, for example, diesel, gasoline, LPG and naphtha.

No gas is recycled from the effluent 7 to the reaction zone 80 of the membrane reactor 30 (i.e., no internal recycle). The system 100 includes no compressor for recycling of gas from the products outlet 30$g$ to the modified gas feed inlet 30$f$. Internal recycle can be eliminated because the modified gas feed 6 has a desirable hydrogen to carbon monoxide ratio to produce desirably heavy hydrocarbons and low light gas. By eliminating internal recycle, capital and operating expenses associated with compression can be avoided and the process complexity is reduced. Furthermore, the elimination of the internal recycle reduces the throughput of the reactor. As a result, the reactor 30 can be reduced in size. Despite the elimination of internal recycle, high single pass conversion of carbon monoxide is possible because of the uniform flow of hydrogen and carbon monoxide from the sweep zone 40 into the reaction zone 80 and the removal of water from the reaction zone.

Suitable water permselective membranes 45 can be selected from zeolite membranes, ceramic membranes, polymeric membranes and composite membranes. Composite membranes include composites of ceramic and polymeric materials, composites of metallic and polymeric materials, and composites of ionic liquids and porous supports. In another embodiment zeolite membranes can be used, for instance Linde type 4A zeolite membranes such as those available from Mitsui Engineering & Shipbuilding Co., Ltd, Japan, and Fraunhofer Institute for Ceramic Technologies and Systems IKTS, Germany. Suitable membranes have a water/carbon monoxide selectivity of at least 10, even at least 100. Suitable membranes have a water permeance of at least 1000 GPU (gas permeation units), even at least 4000 GPU. One GPU is defined as the gas or vapor flow rate through a material per unit area and per unit of pressure difference across the material, with the unit defined as $10^{-6}$ cm$^3$(stp)·cm$^{-2}$·s$^{-1}$·cmHg$^{-1}$. The membrane can be supported by a porous support, such as a ceramic, polymeric or metal support.

A sweep zone gas containing hydrogen ($H_2$) and carbon monoxide (CO) is caused to flow across the permeate side of the membrane at a pressure sufficient to cause hydrogen and CO to pass from the permeate side of the membrane to the reaction zone along the length of the reactor, either continuously or at discrete locations. The sweep zone gas contains high partial pressures of hydrogen gas and CO; and permeation of hydrogen and CO to the reaction zone occurs when the hydrogen and CO partial pressures on the permeate side are higher than the hydrogen and CO partial pressures on the retentate side facing the reaction zone. Not only are hydrogen and CO inhibited from "leaking" out of the reaction zone through the water removal membrane, thus having a negative impact on productivity, but hydrogen and CO are actually added to the reaction zone, thus enhancing the productivity of the reactor. Because the $H_2$ partial pressure difference is higher than the CO partial pressure difference between the sweeping gas and the reaction gas, more $H_2$ is expected to permeate to the reaction zone than CO. Thus, a suitable $H_2$/CO ratio is maintained along the reaction zone length.

In a Fischer-Tropsch (FT) process, typically, the reaction conditions include using a suitable FT catalyst such as an iron-based or cobalt-based catalyst or a mixture of both. In one embodiment, the reaction occurs at a temperature between about 160° C. and about 350° C., even between about 200° C. and about 250° C. In another embodiment, the temperature is kept at about 180-220° C. when cobalt-based catalysts are used and about 250-280° C. when iron-based catalysts are used. The pressure in the reaction zone is between about 1 and about 100 atmospheres, even between about 10 atmospheres and about 30 atmospheres. The partial pressure of water should be lower in the permeate side of the water removal membrane than in the reaction zone for the water to permeate. A syngas-containing sweep zone gas having a $H_2$/CO ratio greater than about 2.0 is used to further reduce the partial pressure of water on the permeate side of the water removal membrane and hence increase the driving force for the water separation. The gaseous hourly space velocity of the reaction is less than about 20,000 volumes of syngas per volume of catalyst per hour.

EXAMPLES

Computer modeling was used to simulate an embodiment using fresh syngas as a sweep zone gas feed in a membrane reactor as illustrated in FIG. 1B. The fresh sweep zone gas feed 3 had a hydrogen to carbon monoxide ratio of 2, and the modified gas feed 6 had a hydrogen to carbon monoxide ratio of 1.6.

A simulation was conducted using software based on Aspen Custom Modeler, commercially available from Aspen Technology Inc., Burlington, Mass. The membrane transport properties, operating conditions and reactor dimensions assumed are listed in Table 1. Reaction kinetics for a cobalt-based FT catalyst containing 7.5 wt % Co and 0.19 wt % Ru on a support containing 80 wt % ZSM-12 zeolite and 20 wt % $Al_2O_3$ was assumed. The simulation was conducted for a single tube-in-tube reactor, with the results multiplied by 50,000, assuming a system of reactors with 50,000 reaction tubes. The syngas ($H_2$/CO=1.6) flow rate per tube was assumed to be 0.9702 lb-mol/hr. Sweep gas ratio is defined as the mole of sweep zone gas per total mole of feed gas.

TABLE 1

| Membrane properties | |
|---|---|
| $H_2O$ permeance | $1.38 \times 10^{-5}$ mol/cm$^2$-bar-sec (4400 GPU) |
| $H_2O/H_2$ selectivity | 50 |
| $H_2O/CO$ selectivity | 125 |
| $H_2O/CO_2$ selectivity | 60 |
| $H_2O/N_2$ selectivity | 150 |
| $H_2O/CH_4$ selectivity | 200 |
| Operating conditions | |
| $H_2$/CO ratio of the reactor feed | 1.6 |
| Pressure | 22 bar (2200 kPa) |
| Temperature | 190° C. |
| Sweep gas ratio | 1.16% |
| Sweep gas pressure | 25 bar (2500 kPa) |
| Tube-in-tube reactor design | |
| Reactor tube outer diameter | 1.66 in (4.2 cm) |
| Reactor tube inner diameter | 1.426 in (3.6 cm) |
| Membrane tube outer diameter | 1.05 in (2.7 cm) |
| Membrane tube inner diameter | 0.83 in (2.1 cm) |
| Reactor length | 60 ft (11 m) |

Figure 3:
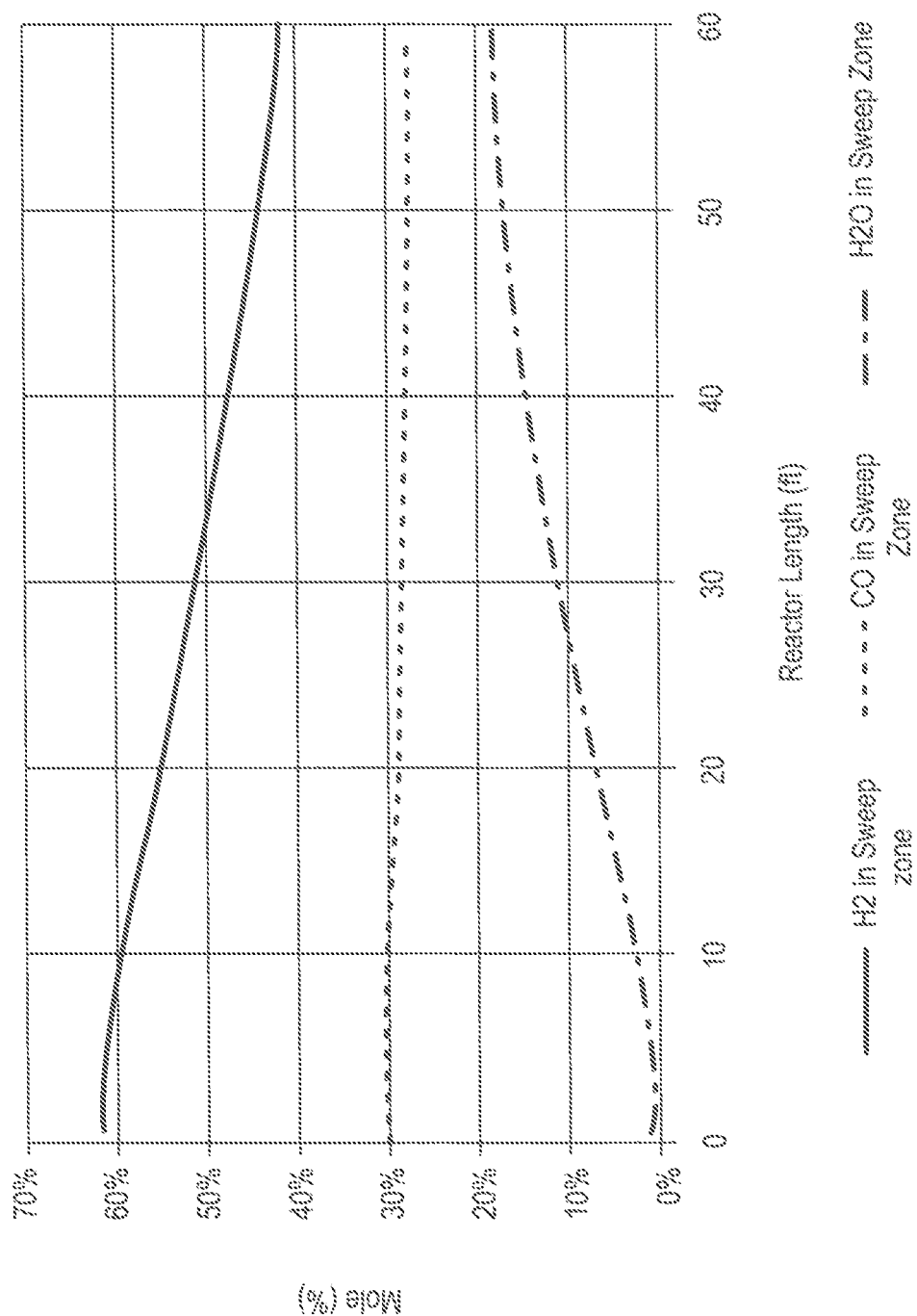
FIG. 3 is a graph of the mole fractions along the length of a Fischer-Tropsch fixed bed reactor for sweep zone gas hydrogen, sweep zone gas carbon monoxide and sweep zone gas water utilizing a system according to one embodiment of the invention.
Figure 4:
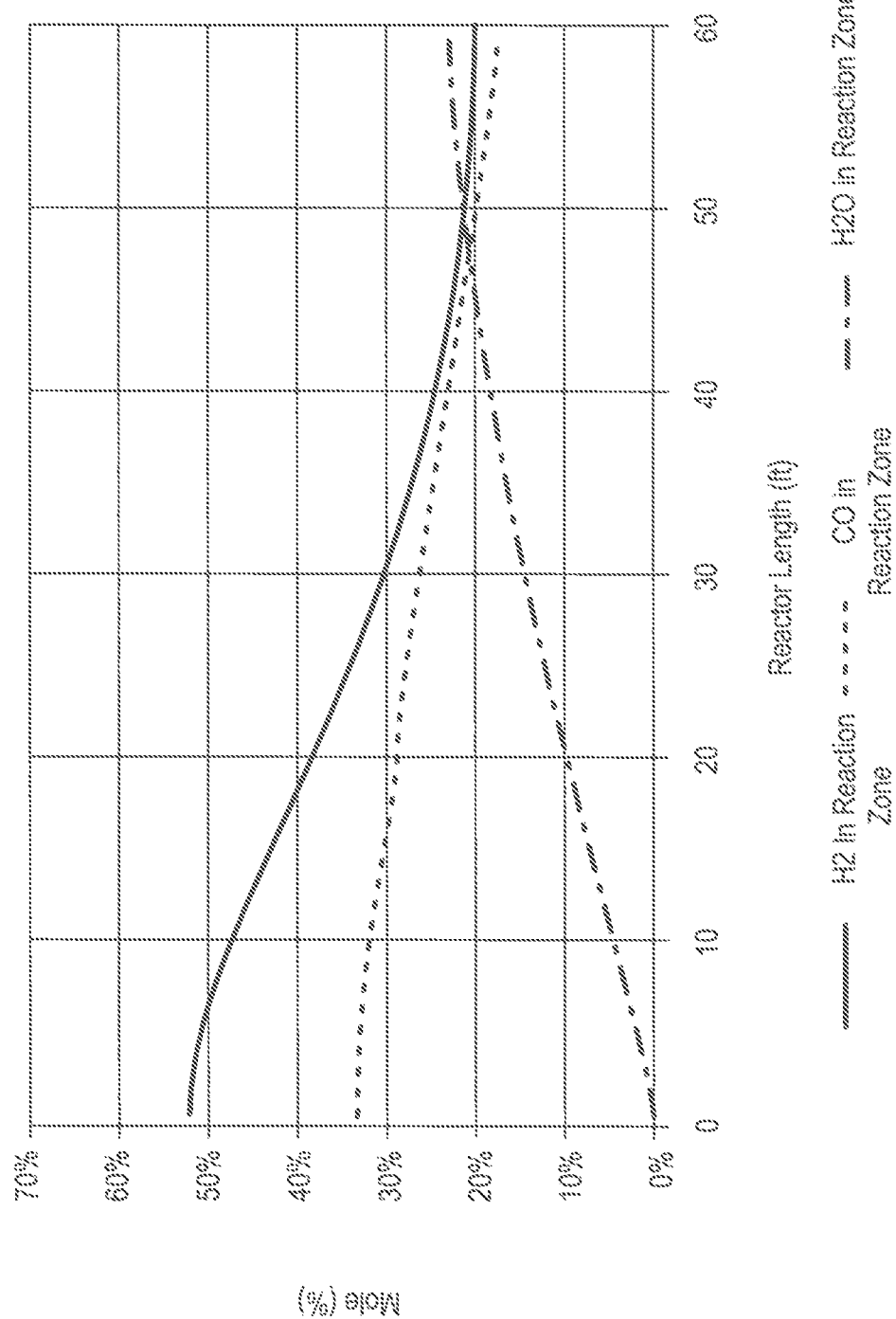
FIG. 4 is a graph of the mole fractions along the length of a Fischer-Tropsch fixed bed reactor for hydrogen, carbon monoxide and water in the reaction zone utilizing a system according to one embodiment of the invention.

Mole fractions changes in the sweep zone in the flow direction are illustrated in FIG. 3. FIG. 4 is a graph of the mole fractions along the length of the membrane reactor for hydrogen, carbon monoxide and water in the reaction zone.

Although both $H_2$ and CO mole fraction decrease along the reactor as $H_2$ and CO reacts to form FT product, the decrease is not as steep as in a conventional FT reactor. The $H_2O$ mole fraction increases along the reactor as $H_2O$ is produced in the reaction zone, but the increase is not as steep as in a conventional FT reactor. Water partial pressure is about 3.6 bar at the products outlet; which is smaller than the water vapor partial pressure that could damage FT catalysts. A higher $H_2$/CO ratio is maintained in the fresh syngas sweep membrane reactor along the reactor length. The higher $H_2$/CO ratio near the downstream end of the reactor is believed to reduce the formation of olefins and oxygenates in the reactor. Reduced formation of olefins may result in lower upgrade costs since downstream hydrotreatment can be avoided or reduced. Reduced formation of oxygenates may result in lower water treatment costs.

Figure 5:
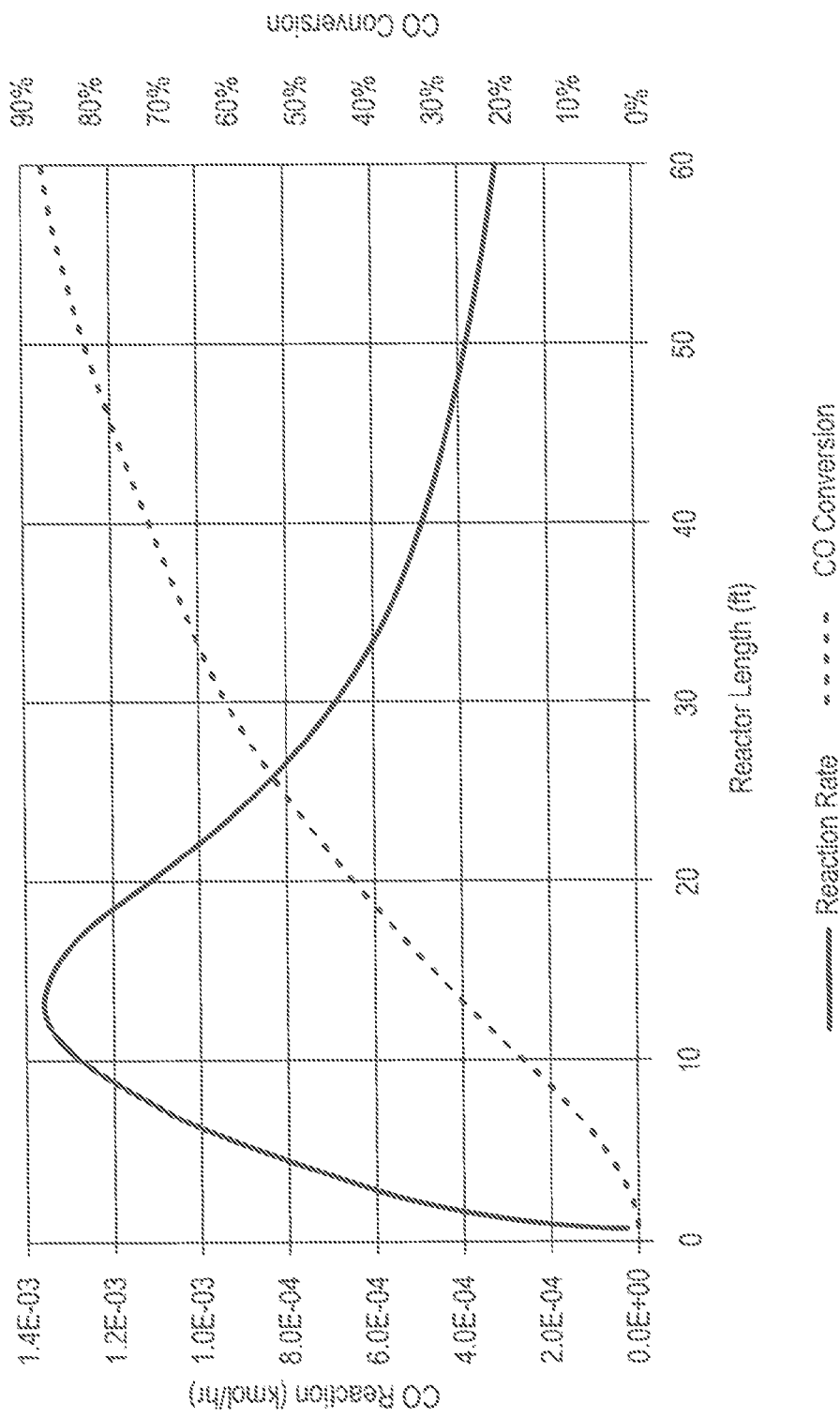
FIG. 5 is a graph of the CO conversion rate and carbon monoxide reaction rate along the length of a Fischer-Tropsch fixed bed reactor utilizing a system according to one embodiment of the invention.

FIG. 5 is a graph of the CO conversion rate and carbon monoxide reaction rate along the length of the membrane reactor. The results indicate that considerably higher CO conversion is achieved for the syngas sweep membrane reactor because $H_2$ and CO permeating from the sweep side and water permeating from the reaction side to the sweep side increases mole fractions of reactants and reduces mole fractions of products; hence kinetics is improved and higher conversion is achieved in a single pass.

Higher levels of single pass CO conversion allow for the elimination of internal recycle, increased hydrocarbon product yields, higher carbon efficiency and lower reactor feed rate. Table 2 lists the benefits of the use of a water removal membrane with syngas sweep zone gas when compared with a reactor not utilizing a membrane and sweep zone gas (also referred to as "non-membrane reactor"). "Product" refers to the amount of produced liquid hydrocarbons. "Recycle ratio" refers to the ratio of recycle stream flow rate to the fresh syngas flow rate. The recycle stream is the stream of unreacted CO, $H_2$, inert gases ($N_2$, $CO_2$) and light hydrocarbons from the reactor outlet after condensing liquid products and water, the recycle stream being recycled to the reactor inlet. "Carbon efficiency" refers to the amount of carbon in the final product divided by the carbon in the system feedstock.

TABLE 2

|  | Syngas sweep membrane reactor |
| --- | --- |
| Reactor length, feet (meters) | 60 (18 m) |
| Number of reactor tubes | 50,000 |
| CO single pass conversion, mol % | 88 |
| Product, barrels per day | 37,883 |
| Recycle ratio | 0 |
| Carbon efficiency, % | 77.0 |
| Reactor feed flow rate, lb-mol/hr | 63459 |
| Water partial pressure at reactor end, bar | 3.4 (340 kPa) |

While in the foregoing specification this invention has been described in relation to certain preferred embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A synthesis gas conversion process comprising:
    (a) providing a reactor comprising:
        i. a sweep zone gas feed inlet;
        ii. a sweep zone gas outlet in fluid communication with the sweep zone gas feed inlet;
        iii. a reaction zone for containing synthesis gas conversion catalyst in which hydrogen and carbon monoxide react to form reaction products including water;
        iv. a products outlet in fluid communication with the reaction zone; and
        v. a membrane having a reactant side contacting the reaction zone and a sweeping side opposite the reactant side;
    (b) passing a sweep zone gas feed comprising hydrogen and carbon monoxide having a hydrogen to carbon monoxide ratio of greater than 2 through the sweep zone gas feed inlet, over the sweeping side of the membrane and out the sweep zone gas outlet wherein hydrogen and carbon monoxide pass from the sweep zone gas feed into the reaction zone from the sweeping side of the membrane and water passes from the reaction zone through the membrane into the sweep zone gas removed from the reactor through the sweep zone gas outlet;
    (c) separating the water from the sweep zone gas removed from the reactor through the sweep zone gas outlet to form a modified gas feed comprising hydrogen and carbon monoxide having a hydrogen to carbon monoxide ratio of less than 1.7;
    (d) contacting the modified gas feed with the synthesis gas conversion catalyst in the reaction zone to form reaction products including water; and
    (e) removing the reaction products from the reactor.

2. The process of claim 1, further comprising reforming methane-containing gas to form the sweep zone gas feed comprising hydrogen and carbon monoxide having a hydrogen to carbon monoxide ratio of greater than 2 in a methane reformer having an outlet connected to the sweep zone gas feed inlet.

3. The process of claim 2, further comprising separating the reaction products into tail gas and nongaseous products after removal from the reactor; and recycling the tail gas to the methane reformer.

4. The process of claim 1, wherein the process includes no recycle of gas from the reaction products to the reaction zone.

5. The process of claim 1, wherein the membrane is selected from the group consisting of zeolite membranes, ceramic membranes, polymeric membranes and composite membranes.

6. The process of claim 1, in which the hydrogen and carbon monoxide react at a single pass carbon monoxide conversion of at least 80 mol % based on the amount of carbon monoxide in the sweep zone gas feed.

7. The process of claim 1, wherein the modified gas feed and the sweep zone gas feed flow co-currently in the reactor.

8. The process of claim 1, wherein the modified gas feed and the sweep zone gas feed flow counter-currently in the reactor.

* * * * *